United States Patent [19]
Frid et al.

[11] Patent Number: 6,159,228
[45] Date of Patent: Dec. 12, 2000

[54] APPLICATOR FOR LUMINAL ENDOPROSTHESES

[76] Inventors: Noureddine Frid, Kerkveldstraat, 190, B-1650 Beersel, Belgium; Mickaël Marianne, 36 Place des Vosges, 54000 Nancy, France

[21] Appl. No.: 09/081,664

[22] Filed: May 20, 1998

[30] Foreign Application Priority Data

May 20, 1997 [BE] Belgium ................................. 9700440
May 19, 1998 [EP] European Pat. Off. .............. 98870114

[51] Int. Cl.⁷ .................................................. A61M 29/00
[52] U.S. Cl. ........................................... 606/198; 606/108
[58] Field of Search .................................... 606/198, 185, 606/108, 194, 190–192; 604/280, 96–104

[56] References Cited

U.S. PATENT DOCUMENTS

| | | |
|---|---|---|
| 4,425,908 | 1/1984 | Simon . |
| 4,503,569 | 3/1985 | Dotter . |
| 4,512,338 | 4/1985 | Balko et al. . |
| 4,580,568 | 4/1986 | Gianturco . |
| 4,655,771 | 4/1987 | Wallsten . |
| 4,665,906 | 5/1987 | Jervis . |
| 4,681,110 | 7/1987 | Wiktor . |
| 4,743,251 | 5/1988 | Barra . |
| 4,795,458 | 1/1989 | Regan . |
| 4,950,227 | 8/1990 | Savin et al. . |
| 4,954,126 | 9/1990 | Wallsten . |
| 5,026,377 | 6/1991 | Burton et al. ........................... 606/108 |
| 5,037,427 | 8/1991 | Harada et al. . |
| 5,061,275 | 10/1991 | Wallsten . |
| 5,067,957 | 11/1991 | Jervis . |
| 5,190,546 | 3/1993 | Jervis . |
| 5,197,978 | 3/1993 | Hess . |
| 5,201,901 | 4/1993 | Harada et al. . |
| 5,226,913 | 7/1993 | Pinchuk . |
| 5,354,309 | 10/1994 | Schnepp-Pesch et al. . |
| 5,395,390 | 3/1995 | Simon . |
| 5,405,377 | 4/1995 | Cragg . |
| 5,458,615 | 10/1995 | Klemm et al. ........................... 606/198 |
| 5,480,423 | 1/1996 | Ravenscroft et al. . |
| 5,534,007 | 7/1996 | St. Germain et al. ................... 606/108 |
| 5,540,712 | 7/1996 | Kleshinski . |
| 5,540,713 | 7/1996 | Schnepp-Pesch et al. . |
| 5,554,181 | 9/1996 | Das . |
| 5,562,725 | 10/1996 | Schmidt et al. . |
| 5,562,728 | 10/1996 | Lazarus et al. . |
| 5,575,818 | 11/1996 | Pinchuk . |
| 5,597,378 | 1/1997 | Jervis . |
| 5,630,840 | 5/1997 | Mayer . |
| 5,643,278 | 7/1997 | Wijay . |
| 5,643,339 | 7/1997 | Kavteladze et al. . |
| 5,645,559 | 7/1997 | Hachtman et al. . |
| 5,674,277 | 10/1997 | Freitag . |
| 5,741,333 | 4/1998 | Frid . |
| 5,843,027 | 12/1998 | Stone et al. ............................. 606/194 |
| 5,851,210 | 12/1998 | Torossian ................................ 606/198 |
| 6,007,573 | 12/1999 | Wallace et al. ........................... 623/1 |
| 6,042,589 | 3/2000 | Marianne ................................ 606/108 |

FOREIGN PATENT DOCUMENTS

| | | |
|---|---|---|
| 1205743 | 9/1970 | European Pat. Off. . |
| 0730848 | 2/1996 | European Pat. Off. . |
| 0740928 | 3/1996 | European Pat. Off. . |
| 0744164 | 5/1996 | European Pat. Off. . |
| WO 9219310 | 11/1992 | WIPO . |
| WO 9530385 | 11/1995 | WIPO . |
| WO 9531945 | 2/1996 | WIPO . |
| WO 9713475 | 4/1997 | WIPO . |

*Primary Examiner*—Michael Buiz
*Assistant Examiner*—Jonathan D. Goldberg
*Attorney, Agent, or Firm*—Roylance, Abrams, Berdo & Goodman, L.L.P.

[57] ABSTRACT

Applicator for luminal endoprostheses Device for medical use, in particular device for positioning a radially extendable luminal endoprosthesis (1) in an anatomical conduit, the device comprising a tubular sheath and having a distal end (4) and a proximal end (5), the sheath including, near the distal end (4), at least one zone (12, 13) whose radiopacity is lower than the radiopacity of an adjacent zone.

10 Claims, 3 Drawing Sheets

6,159,228

APPLICATOR FOR LUMINAL ENDOPROSTHESES

FIELD OF INVENTION

The invention relates to applicators for radially expandable luminal endoprostheses and more particularly for vascular endoprostheses, and especially stents.

Since the work done by C. DIDCOTT on the dilation and the support of anatomical conduits, the concept of dilatable endoprostheses has enjoyed great success, and attempts have been made to apply this concept to blood vessels of ever finer dimensions.

One of the most remarkable breakthroughs in this field concerns in particular cardiac surgery and the reduction of aneurysms.

One consequence of the positioning of dilatable endoprostheses in conduits which are more and more difficult to access has been increasing demands on the part of practitioners, both as regards the quality of the products brought onto the market, and also their ease of use.

The reason is that given the complexity of the manipulations, the margin of tolerance as regards the positioning is reduced.

One of the problems confronting the practitioner is that of exact positioning of the dilatable prostheses in situ.

BACKGROUND OF THE INVENTION

Applicator devices for endoprostheses are known which include a sheath in which the future prosthesis is placed in the radially contracted state, prior to its implantation. A support rod passes through the sheath, inside this same prosthesis. To make them easier to trace, some applicators include beads or rings of radiopaque material, in particular of gold or platinum (as described e.g. in U.S. Pat. No. 5,201,901) or tantalium (U.S. Pat. No. 5,480,423), which are fitted on the support rod, at the distal and proximal ends of the prosthesis in its radially contracted shape. Metallic markers may also be fitted on the outer sheath, as in U.S. Pat. No. 5,026,377. The disadvantage of these markers lies in their relative axial and radial bulk, in their price and in the fact that the operator has to fully perfect the procedure for deployment of the endoprosthesis, whose length, when contracted, can be very considerable (up to 300%) compared to its length when deployed. In addition, the variation in length is also a function of the type and the diameter of the endoprosthesis.

SUMMARY OF THE INVENTION

The object of the invention is to develop a comparatively cheap device for precise and effective positioning of luminal endoprostheses.

The subject of the invention is a device for positioning a radially extendable luminal endoprosthesis in an anatomical conduit, the device comprising a tubular sheath and having a distal end and a proximal end, it being possible for a radially extendable endoprosthesis to be inserted in this sheath in a radially contracted shape, in which device the sheath is made up of at least one layer of material and comprises several zones,
a radiopaque material is incorporated in at least one component of at least one of the layers in at least one of the zones of the sheath, this at least one layer extending along most of the distal end of this sheath,
the said sheath comprises, near the distal end, at least one zone whose radiopacity is lower than from the radiopacity of an adjacent zone, and
at least one boundary limit between two zones of different radiopacity is disposed at a predetermined distance from the distal end, corresponding to a predetermined position adopted by one of the ends of the endoprosthesis when it is in place in its radially extended shape.

The device of the invention advantageously comprises two boundary limits between zones of different radiopacity, each of these boundary limits being disposed at a distance from the distal end of the device corresponding to the predetermined position of one end of the endoprosthesis when it is in place in its radially extended shape.

It can comprise at least two zones whose radiopacity differs from the radiopacity of an adjacent zone.

The sheath can comprise a framework, which is preferably braided.

The sheath preferably comprises at least one layer of extruded material.

The device advantageously comprises a pusher for supporting the endoprosthesis, and a locking member able to react when the sheath undergoes a relative displacement, with respect to the pusher, by a length corresponding to that separating the distal end of the device and a boundary limit between two zones of different radiopacity.

The invention also relates to a device for medical use, intended to be introduced into an anatomical conduit, the device comprising a tubular sheath and having a distal end and a proximal end, in which device the sheath is made up of at least one layer of material and comprises several zones, said layer extending along most of the distal length of this sheath,
a radiopaque material is incorporated in at least one component of at least one of the layers in at least one of the zones of the sheath,
the said sheath comprises, near the distal end, at least one zone whose radiopacity is lower than the radiopacity of an adjacent zone, and
at least one boundary limit between two zones of different radiopacity is disposed at a predetermined distance from the distal end.

The invention furthermore relates to a method for manufacturing a sheath for a device, the method comprising the following operations setting up a mandrel,
constructing on this mandrel a thermoplastic matrix which includes, alternately, at least one segment of defined radiopacity and at least one segment of different radiopacity,
engaging a heat-shrinkable collar on the matrix,
subjecting the whole arrangement to a thermal treatment which is able to trigger the radial shrinkage of the collar and the fusion of the segments of the matrix,
removal of the collar and of the mandrel.

This method preferably comprises one of the following operations, or both operations:

prior to thermal treatment, insertion of an internal sleeve with a low coefficient of friction, placed beneath the matrix, and
prior to thermal treatment, insertion of a framework, placed beneath the matrix.

One advantage of the invention is that the practitioner can accurately evaluate the position e.g. of an endoprosthesis during the implantation procedure.

Another advantage is that the length of the endoprosthesis can be adapted, almost to the millimetre, to the lesion which is to be treated.

The monitoring of a patient is also made considerably easier, and any side effects can be better detected.

Practitioners can focus their attention on other fundamental aspects of the operation to be carried.

The markers are incorporated fully within the applicator, without protruding, thus affording enhanced manoeuvrability and very precise calibration.

The time taken for putting the endoprosthesis into place is reduced by virtue of the absence of trial and error manoeuvres, and this is all to the benefit of the patient's health and the cost of the operation.

The detection marker is very clear on the monitoring screen and can even include supplementary codes facilitating handling.

BRIEF DESCRIPTION OF THE DRAWINGS

Other features and advantages of the invention will be evident from the description of specific embodiments, with reference being made to the attached figures, of which

DESCRIPTION OF THE EMBODIMENTS

One embodiment of a device according to the invention will be described first with reference to FIGS. 1, 2 and 3.

Figure 1:
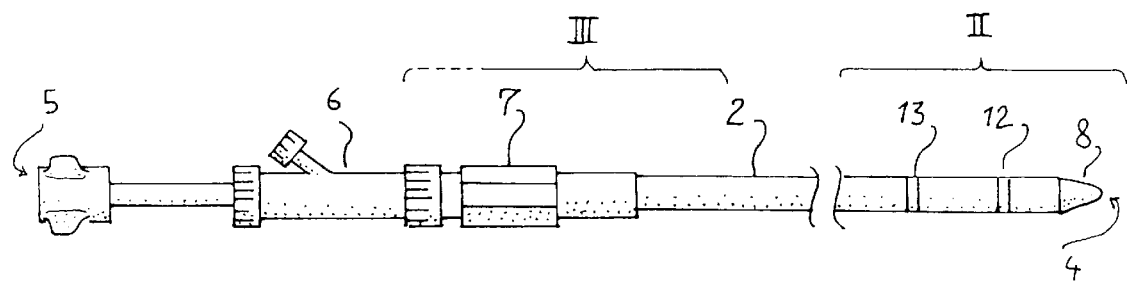
FIG. 1 is a general view with interruption, parallel to the axis of a device according to the invention.
Figure 2:
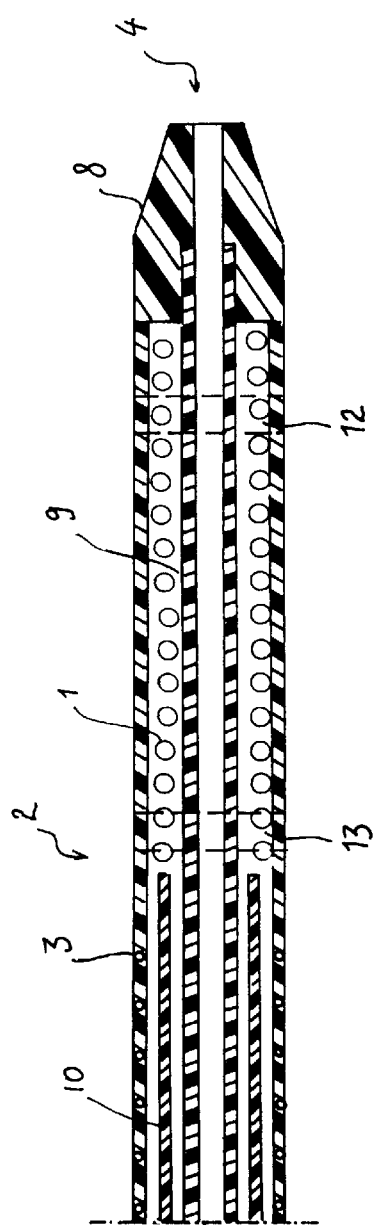
FIGS. 2 and 3 are interrupted longitudinal sections through the distal and proximal ends, respectively, of a device according to the invention, enclosing a radially expandable endoprosthesis.

FIG. 1 shows the general appearance of the device.

The device as a whole is intended for releasing expandable luminal endoprostheses in an anatomical conduit (and in particular an arterial conduit). An endoprosthesis 1 is inserted in its radially contracted shape into a sheath 2 which is here reinforced by a framework 3, in this case braided. Other types of frameworks such as rings or incised cylinders can be used.

The length of the sheath 2 is such that its distal end 4 can be brought, by way of a natural orifice or an incision, to the site of a lesion that is to be treated.

The operator manipulates the device by acting on its proximal end 5, on which various accessories 6 can be fitted by way of a connector or Luer 7.

The distal end 4 of the sheath 2 is capped with a non-traumatizing tip 8 which facilitates guidance and positioning. As can be seen in FIGS. 2 and 3, and in particular in FIG. 3, this tip 8 is connected via a hollow rod 9 to a flexible pusher 10, for example of polyamide.

The release manoeuvre is effected as follows: with the proximal end of the flexible pusher 10 being held in place by way of a rigid pusher 11 (which is here made of stainless steel), the operator pulls the sheath 2, which slides and gradually frees the endoprosthesis 1 from its radial constraint.

At this point, the dexterity and experience of the operator play a crucial role since, to help determine the correct positioning of the endoprosthesis 1, he has only a two-dimensional image on a screen, on which the travel of the sheath 2 is recorded.

The dilation of the endoprosthesis 1 entails a concomitant decrease in its length. The operator must therefore have considerable practical experience to be able to judge the ideal release position. Moreover, each type of endoprosthesis, depending on its mechanical characteristics, and in particular its nominal diameter, has a different factor of shortening.

The device according to the invention comprises two zones whose radiopacity differs from the radiopacity of the adjacent zones, namely the radio-detectable zones 12, 13 incorporated in the sheath 2.

Figure 4:
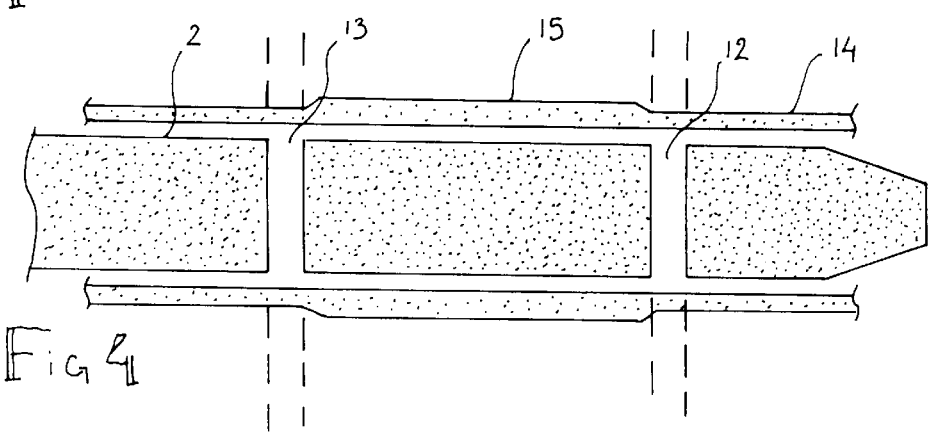
FIG. 4 is a diagrammatic view of an in situ device as shown on a monitoring screen.
Figure 5:
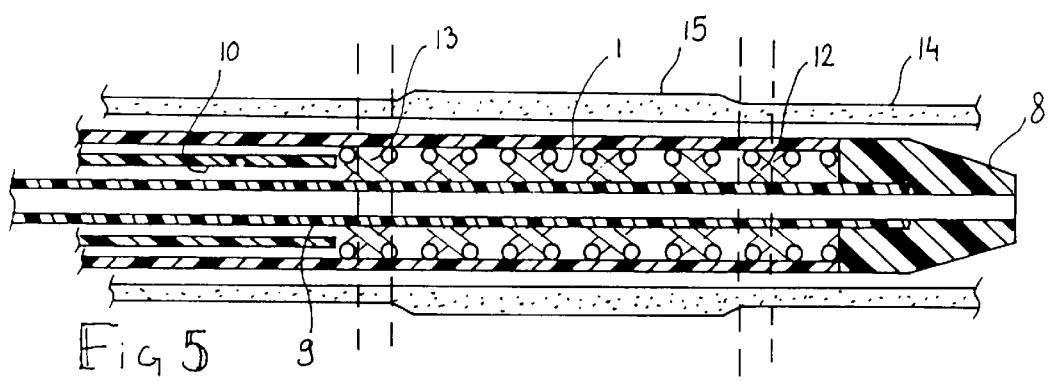
FIGS. 5 and 6 are diagrammatic views in cross-section representing stages in the positioning of an endoprosthesis using a device according to the invention.
Figure 6:
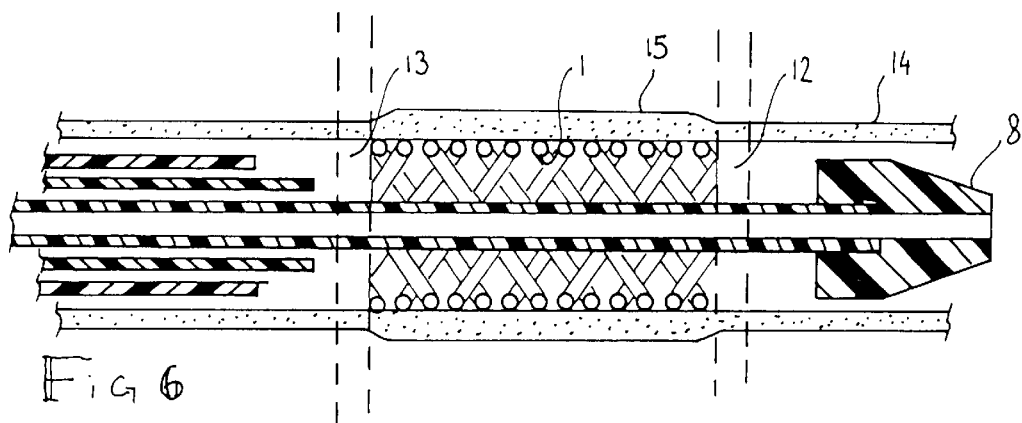

The release manoeuvre using the device according to the invention is performed as described schematically with reference to FIGS. 4, 5 and 6.

FIG. 4 is a diagrammatic representation of an image of the distal end 4 of the device in place in an anatomical conduit, the image being seen on an operating screen.

The symbols in FIG. 4 are used to illustrate the principle of the invention, but do not necessarily correspond to the concrete reality of the representation on a monitoring screen.

An anatomical conduit 14 with a lesion 15 to be treated appears in grey in the figure.

The sheath 2 also appears in grey, on account of the presence, in one of its layers, of a radiopaque material (for example a barium salt such as $BaSO_4$).

The two radio-detectable zones 12, 13, here formed from a segment of the sheath 2 whose layers are without radiopaque charge, appear in the form of two clear and easily identifiable discontinuities.

It then suffices for the operator to manoeuvre the device via its proximal end 5 so as to bring these two radio-detectable zones 12, 13 into line with the lesion 15 (as is shown in FIG. 5). By holding the rod 9 in this position, the operator slides the sheath 2 backwards so that the endoprosthesis 1 deploys in the anatomical conduit 14, precisely adopting the position defined beforehand by the radio-detectable zones 12, 13.

The rod 9 and the non-traumatizing tip 8 are then withdrawn through the passage freed by the endoprosthesis 1.

As is illustrated in FIG. 6, the length of the deployed endoprosthesis 1 differs notably from its initial length when radially contracted.

Because the endoprosthesis 1 is released in its ideal position, the trial and error manoeuvres are reduced to a bare minimum, and the operator is able to concentrate on more tricky aspects of the operation.

Figure 3:
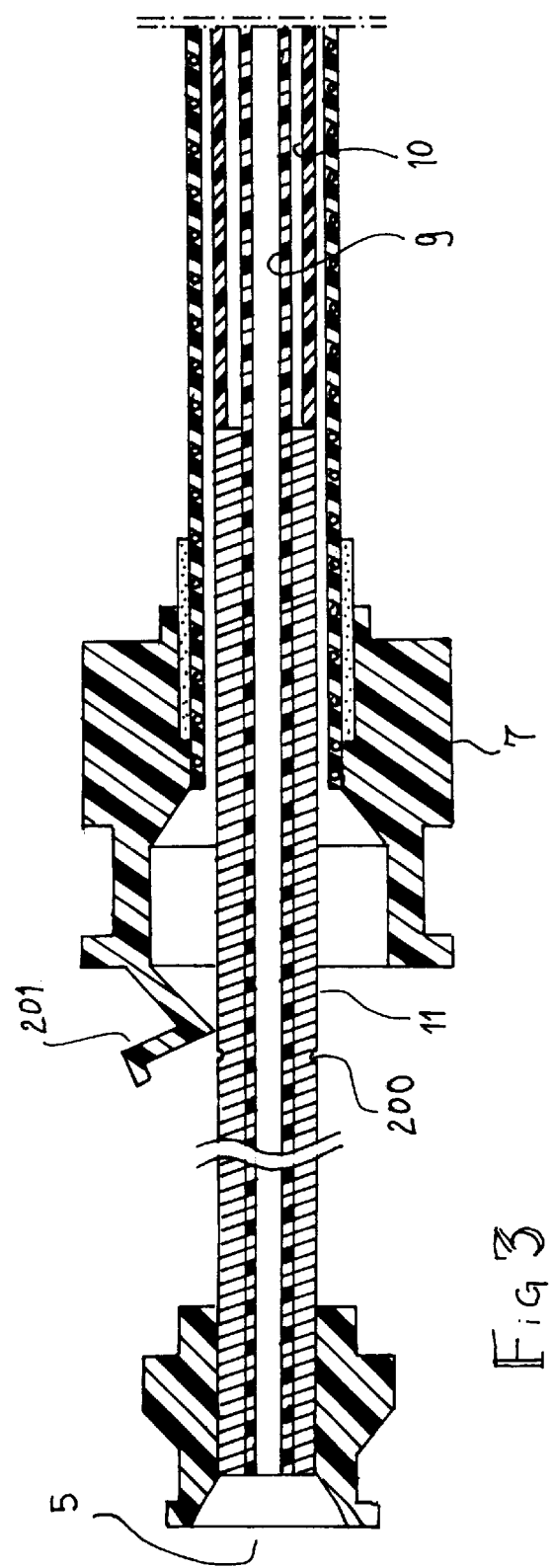

As can be seen in FIG. 3, a groove 200 is disposed on the pusher 11. This groove 200, cooperating with a stud 201 situated on the Luer 7, forms a locking device which, at the moment of disengagement of the sheath 2, provides the operator with a tactile indication of the start and/or end of the positioning of the endo-prosthesis 1.

The margin of error in positioning being clearly smaller than in the case of the known devices, the length of the endoprosthesis 1 can be calculated very precisely, and this permits better monitoring of the patient after the operation.

The marking of the sheath 2 allows for a multiplicity of variants which do not depart from the scope of the invention. Thus, radio-detectable zones such as the zones 12, 13 described with reference to FIG. 4 as "radio-invisible" can also be designed as radiopaque zones appearing by contrast on the path of a radio-invisible sheath or with a radiopacity different from that of the radio-detectable zones. One of the zones 12, 13 can also be divided in two in order to provide a useful indication for the operator.

Finally, these two zones 12, 13 can be joined together so that a single segment appears on screen, the length and position of which segment correspond to those of the deployed endoprosthesis 1. Depending on the characteristics of shortening of the endoprosthesis 1, one of the zones 12, 13 may optionally be omitted.

For the concrete realization of the described device, the presence of radio-detectable zones on the sheath 2 must not normally lead to appreciable variation in the internal or external diameter of this sheath 2, and, optimally, must not introduce any interruption of continuity in the mechanical characteristics of the device (flexibility, buckling resistance, etc.).

Figure 7:
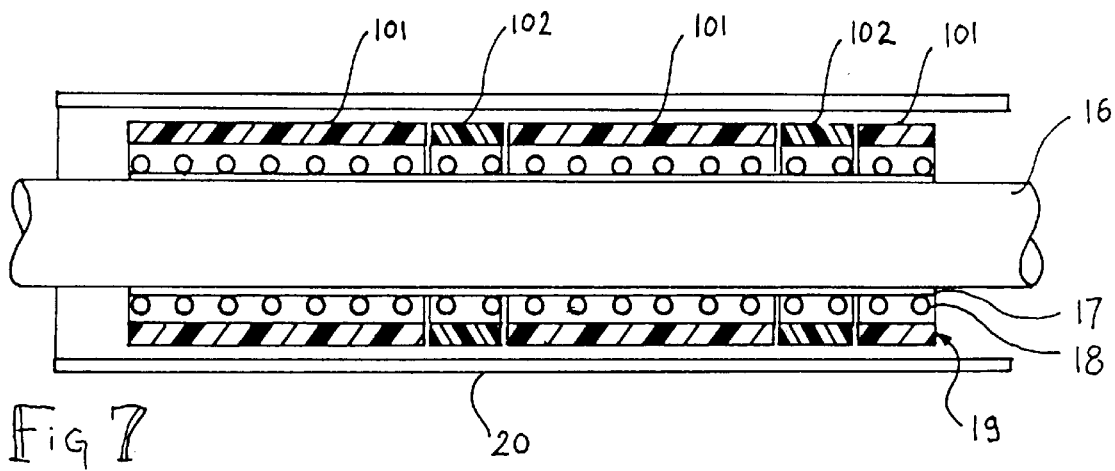
FIGS. 7, 8 and 9 are diagrammatic views in longitudinal section representing different stages in a method for manufacturing a sheath of a device according to the invention.
Figure 8:
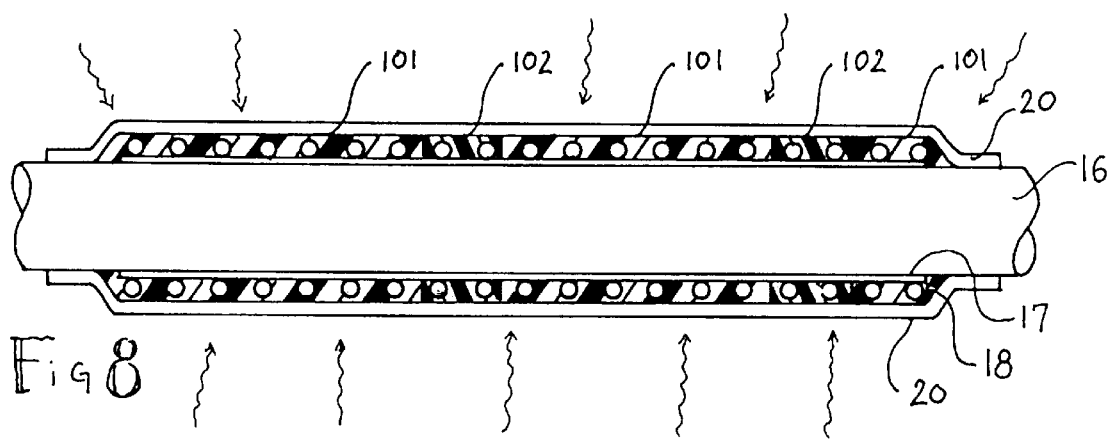
Figure 9:
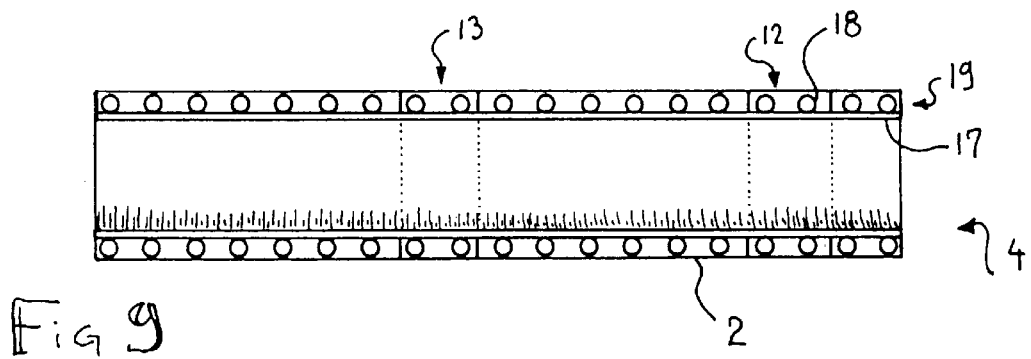

The method for manufacturing a sheath 2 for a device according to the invention, described hereinafter with reference to FIGS. 7 to 9, is able to satisfy these requirements.

In the case of a device intended for the positioning of an endoprosthesis, one begins by carrying out, for an endoprosthesis of given type and given diameter, a calibration which allows one to determine precisely the relative positions of the radio-detectable zones 12, 13 and of the distal end 4 of the sheath 2 corresponding to the distal end 4 of the device.

The elements of the sheath 2 are assembled using a calibrated mandrel 16, made for example of a straightened bar of stainless steel. This mandrel 16 guarantees great precision in the internal diameter of the sheath 2, which is an important point for the subsequent passage of accessories.

The various components of the sheath 2 are mounted on the mandrel 16, namely:

an internal sleeve 17 with a low coefficient of friction (made of PTFE, for example), the external surface of which is treated in such a way as to permit its adhesion to the other components of the sheath 2;

a framework 18, which is preferably a metal braid.

The braided configuration confers an excellent resistance to torsion and compression, as well as good resistance to kinking. In addition, the sheath thus strengthened is very flexible, which allows it to pass through very sinuous arterial systems. Excellent characteristics have been obtained using a braid comprising 16 filaments of stainless steel with a diameter of 50 $\mu$m.

The sheath 2 includes a tubular matrix 19 formed from segments of thermoplastic materials, for example a mixture of rigid polymer, for example polyamide and elastomer, for example polyether-block-amide, sold under the trade name PEBAX™.

This matrix 19 is formed by juxtaposition of extruded segments 101, 102.

Some of these segments (for example segments 101) comprise a charge of radiopaque material; interposed between these there are other segments (segments 102) which are without radiopaque charge or which have a level of radiopacity contrasting with that of the segments 101.

The segments 102 can also consist of gaps between the segments 101.

Matrix segments made of thermoplastic material and charged with different levels of a radiopaque material (or, if preferred, without a radiopaque charge) are engaged at predetermined intervals on the mandrel 16.

This assembly is covered with a collar 20 of heat-shrinkable material and then undergoes heating to a temperature of between 200 and 300° C. (FIG. 8).

This heating brings about both the fusion of the matrix 19 and the shrinkage of the collar 20, which in this way exerts a radial compression on the matrix 19 during fusion. After this operation, the matrix 19 has a uniform thickness, practically without any interruption of continuity at the level of the radio-detectable zones 12, 13, and is integral with the framework 18.

The collar 20 is made of fluorine material and for this reason does not adhere to the matrix 19. In addition, it ensures that the heat is confined in the sheath 2, and this provides for the homogeneity of the whole assembly.

After cooling, the collar 20 is withdrawn.

The position of the end of the sheath 2 corresponding to the distal end 4 of the device is determined precisely with respect to that of the radio-detectable zones 12, 13. The assembly of the device is traditionally completed by over-moulding of the Luer 7, the introduction of the rod 9, the pushers 10 and 11, the endoprosthesis 1, the non-traumatizing tip 8, etc.

It goes without saying that the manufacturing procedure can comprise a series of variants which do not depart from the spirit of the invention. In particular, the framework 18 may not extend as far as the distal end of the sheath 2, thereby conferring flexibility to the end of the device.

In addition, the radiopaque charge material can be disposed in one or other layer of the sheath 2.

Although the tubular sheath has been described in relation to the device for the positioning of a luminal endoprosthesis according to the invention, it can also fulfill an important role in other therapeutic applications, for example the injection of contrast media into the organism in order to trace lesions.

In this case, the radio-detectable markings made during the manufacture of the sheath can permit precise detection of bifurcations or of blood vessels in planes perpendicular to the axis of the sheath.

What is claimed is:

1. A device for positioning a radially extendable luminal endoprosthesis in an anatomical conduit, the device comprising:

a distal tip;

a tubular sheath, positioned behind the distal tip, and having a distal end and a proximal end, the sheath defining an internal chamber for a radially extendable endoprosthesis to be inserted in the sheath in a radially contracted shape prior to positioning, the sheath comprising at least one layer of material and having several zones;

a sliding device, adapted to slide the sheath with respect to the distal tip to open the chamber for releasing the endoprosthesis from the internal chamber into an anatomical conduit; and a radiopaque material incorporated in at least one component of at least one of the layers in at least one of the zones of the sheath, said at least one layer extending along a portion of the distal end of the sheath, such that the sheath comprises, near the distal end, at least one zone whose radiopacity is lower than the radiopacity of an adjacent zone, and at least one boundary limit between two zones of different radiopacity, which is disposed at a predetermined axial distance from the distal end and corresponds to a position at which one of the ends of the endoprosthesis is to be located when the endoprosthesis is released to assume a radially extended shape.

2. A device according to claim 1, further comprising two of said boundary limits between zones of different radiopacity, each of said boundary limits being disposed at a respective distance from the distal end of the device taken along the longitudinal axis of the device and corresponding to a position at which a respective end of the endoprosthesis is to be located when the endoprosthesis is released to assume said radially extended shape.

3. A device according to claim 1, comprising at least two zones whose radiopacity differs from the radiopacity of an adjacent zone.

4. A device according to claim 1, wherein the sheath comprises a framework.

5. A device according to claim 2, wherein the sheath comprises a framework.

6. A device according to claim 5, wherein the framework is braided.

7. A device according to claim 1, wherein the sheath comprises at least one layer of extruded material.

8. A device according to claim 2, wherein the sheath comprises at least one layer of extruded material.

9. A device according to claim 1, further comprising a pusher for supporting the endoprosthesis, and a locking member, adapted to provide an indication when the sheath undergoes a relative displacement, with respect to the pusher, by a length corresponding to that separating a distal end of the device and a boundary limit between two zones of different radiopacity.

10. A device for medical use, adapted to be introduced into an anatomical conduit, the device comprising:

a distal tip;

a tubular sheath, positioned behind the distal tip and defining an internal chamber, the sheath comprising a distal end and a proximal end, at least one layer of material, and a plurality of zones;

a sliding device, adapted to slide the sheath with respect to the distal tip to open the internal chamber;

a radiopaque material, incorporated in at least one component of at least one of the layers in at least one of the zones of the sheath, said layer extending along a portion of the distal end of the sheath, such that the sheath comprises, near the distal end, at least one zone whose radiopacity is lower than the radiopacity of an adjacent zone, and at least one boundary limit between two zones of different radiopacity which is disposed at a predetermined distance from the distal end taken along the longitudinal axis of the device; and a pusher for supporting an endoprosthesis, and a locking member, adapted to provide an indication when the sheath undergoes a relative displacement, with respect to the pusher, by a length corresponding to that separating a distal end of the device and said boundary limit.

* * * * *